United States Patent
Gylfason et al.

(10) Patent No.: US 10,209,180 B2
(45) Date of Patent: Feb. 19, 2019

(54) SENSOR DEVICE AND A METHOD OF DETECTING A COMPONENT IN GAS

(71) Applicants: Kristinn B. Gylfason, Solna (SE); Hans Sohlström, Stockholm (SE); Floria Ottonello Briano, Stockholm (SE); Göran Stemme, Lidingö (SE)

(72) Inventors: Kristinn B. Gylfason, Solna (SE); Hans Sohlström, Stockholm (SE); Floria Ottonello Briano, Stockholm (SE); Göran Stemme, Lidingö (SE)

(73) Assignee: SenseAir AB, Delsbo (SE)

( * ) Notice: Subject to any disclaimer, the term of this patent is extended or adjusted under 35 U.S.C. 154(b) by 0 days.

(21) Appl. No.: 15/577,685

(22) PCT Filed: Jun. 27, 2016

(86) PCT No.: PCT/SE2016/050631
§ 371 (c)(1),
(2) Date: Nov. 28, 2017

(87) PCT Pub. No.: WO2017/003353
PCT Pub. Date: Jan. 5, 2017

(65) Prior Publication Data
US 2018/0164208 A1     Jun. 14, 2018

(30) Foreign Application Priority Data
Jun. 29, 2015 (SE) .................................... 1550898

(51) Int. Cl.
*G01N 21/35* (2014.01)
*G01N 21/01* (2006.01)
(Continued)

(52) U.S. Cl.
CPC .......... *G01N 21/3504* (2013.01); *G01N 21/01* (2013.01); *G02B 6/136* (2013.01)

(58) Field of Classification Search
CPC ..... G01N 21/01; G01N 21/3504; G02B 6/136
See application file for complete search history.

(56) References Cited

U.S. PATENT DOCUMENTS

| 2008/0044126 A1* | 2/2008 | Costa | G02B 6/1228 |
|---|---|---|---|
| | | | 385/14 |
| 2014/0264030 A1 | 9/2014 | Lin et al. | |
| 2015/0036975 A1 | 2/2015 | Burek et al. | |

FOREIGN PATENT DOCUMENTS

| WO | WO 2006/008447 A1 | 1/2006 |
|---|---|---|
| WO | WO 2008/125797 A1 | 10/2008 |

OTHER PUBLICATIONS

X. Zhou et al., "On-Chip Biological and Chemical Sensing with Reversed Fano Lineshape Enabled by Embedded Microring Resonators." IEEE Journal of Selected Topics in Quantum Electronics, vol. 20, No. 3, pp. 1-10, May/Jun. 2014.
(Continued)

*Primary Examiner* — Mark R Gaworecki
(74) *Attorney, Agent, or Firm* — Blank Rome LLP

(57) ABSTRACT

A sensor device comprising a planar substrate defining a substrate plane and a waveguide for guiding an electromagnetic wave. The waveguide extends in a length direction in a waveguide plane parallel to the substrate plane and has a width and a height, wherein the width to height ratio is more than 5. The height of the waveguide is less than the wavelength of the electromagnetic wave. The waveguide is supported on the substrate by a support structure extending from the substrate to the waveguide, along the length direction of the waveguide, having a width which is smaller than the width of the waveguide. The invention further relates to a method of detecting a component in gas and a method of fabricating a sensor device.

30 Claims, 6 Drawing Sheets

(51) Int. Cl.
   *G02B 6/136* (2006.01)
   *G01N 21/3504* (2014.01)

(56) References Cited

OTHER PUBLICATIONS

P.T. Lin et al., "Air-Clad Silicon Pedestal Structures for Broadband Mid-Infrared Microphotonics," Optics Letters, vol. 38, No. 7, pp. 1031-1033, Apr. 1, 2013.
P.T. Lin et al., "Chip-Scale Mid-Infrared Chemical Sensors Using Air-Clad Pedestal Silicon Waveguides," Lab on a Chip, Lap Chip, vol. 13, pp. 2161-2166, 2013.

* cited by examiner

SENSOR DEVICE AND A METHOD OF DETECTING A COMPONENT IN GAS

TECHNICAL FIELD

The invention relates to a sensor device comprising a waveguide for guiding an electromagnetic wave, and to a method of detecting a component in a fluid such as gas.

BACKGROUND

Optical sensing using the absorption bands of various gases in the visible or infrared (IR) wavelength range is an established method. The absorption may be measured in cavities with mirrors, so as to achieve an effective interaction length which is longer than the physical size of the cavity. This approach is limited by the optical losses in the mirrors. For IR, the source is often a broadband incandescent lamp. To get a spectral resolution, optical spectral analysis is then needed. Detectors can be thermal or semiconductor based photon detectors.

To make sensitive devices with a long optical path-length, either high quality mirrors must be used or the physical path, and hence the device size, must be long. For many applications, low gas flows and the large volume of the gas chamber limit the response speed of the sensor.

US 2014/0264030 A1 describes methods and apparatus for mid infrared sensing.

WO 2008/125797 A1 describes waveguide devices using evanescent coupling between waveguides and grooves.

SUMMARY OF INVENTION

It is an object of the present invention to reduce the shortcomings of prior art. In particular, it is an object to provide a sensor device which may be small while maintaining a sufficient sensitivity to detect components in gas.

Thus the present invention relates to a sensor device comprising;
a planar substrate defining a substrate plane
a waveguide for guiding an electromagnetic wave, the waveguide extending in a length direction in a waveguide plane parallel to the substrate plane, the waveguide having a width in the waveguide plane in a direction perpendicular to the length direction, and a height out of the waveguide plane in a direction perpendicular to the length direction, wherein the width to height ratio is more than 5,
wherein the height of the waveguide is less than the wavelength of the electromagnetic wave, and
wherein the waveguide is supported on the substrate by a support structure extending from the substrate to the waveguide, along the length direction of the waveguide, having a width which is smaller than the width of the waveguide, at the point of support of the waveguide,
and wherein the width of the waveguide is varied along the length direction of the waveguide,
and wherein the width of the support structure varies correspondingly along the length direction of the waveguide.

Thus a simple way of varying the dimensions of the support structure is provided, which also makes it possible to reduce the width of the support structure to the point when the support structure is removed. Thus the support may be tailored along the length of the waveguide. A gradual variation of the width of the support structure further has the advantage of reducing reflections of the electromagnetic wave propagating in the waveguide.

Thereby a sensor device is provided which may be miniaturized while maintaining a good sensitivity to detect components in gas. The features of the waveguide provide for guiding an electromagnetic wave, having an evanescent field outside the waveguide core. The device may be fabricated with planar microfabrication technology with reduced optical losses, due to the dimensional features of the waveguide and the support. The optical losses may be reduced since the planarity of the upper surface of the waveguide may be very well controlled, while losses on lateral side surfaces may be reduced due to the high width to height ratio.

The width to height ratio may be more than 10 or more than 20. The width of the support structure at the point of support of the waveguide may be less than half of the width of the waveguide, less than ¼ of the width of the waveguide or less than ¹⁄₁₀ of the width of the waveguide. Preferably the width of the support structure at the point of support of the waveguide is small to reduce optical losses through the support structure. The support structure may have a shape with a cross sectional width which decreases from the support to the waveguide, to make the support structure more mechanically rigid.

The waveguide may be supported along at least a first portion of the length direction, wherein the width of the waveguide and thus the support is decreased such that the waveguide is free hanging along at least a second portion of the length direction.

Thus a larger portion of the waveguide may be subjected to surrounding gas, and any optical losses through the support may be reduced.

A useful method for production of the waveguide and the support structure is to use etching. The repeatability when using etching is limited. Thus, there is a limit for the smallest possible dimension of the support structure in the etching direction. As a way to reduce the contact area between the support structure and the waveguide the sensor device may be arranged with the waveguide free hanging along a plurality of portions of the length direction, so that a plurality of support pillars is formed, wherein the distance from the center of a support pillar to the center of an adjacent support pillar varies along the length direction. By having the center-to-center distance varying, unwanted constructive or destructive interferences between the propagating wave and the waves reflected at the supports may be avoided. The center-to-center distance of the supports may be randomized.

The device may comprise means to apply a force to the free hanging portion of the waveguide such that to deflect the waveguide.

Thus the electromagnetical wave propagating through the waveguide may be modulated by the deflection of the waveguide. The force may be provided by applying an electrical potential between the substrate and the waveguide, at least at the free hanging second portion of the waveguide, such that to deflect the waveguide with respect to the substrate. Alternatively, the force may be applied by thermal actuation, piezoelectric actuation etc.

The waveguide may comprise at least one gap along the length direction of the waveguide, the at least one gap being less than the wavelength of the electromagnetic wave, preferably less than ⅕ or less than ¹⁄₁₀ of the wavelength of the electromagnetic wave.

Thus the waveguide may be provided with a thermal and/or electrical hinder which still permits the transmission of electromagnetic radiation with low loss. This may be used to obstruct the propagation of thermal or electrical disturbances from one part of the waveguide to another part of the waveguide.

The device may comprise a thermal source of radiation positioned such that to couple an electromagnetic wave from the thermal source of radiation into the waveguide, the thermal source of radiation having an extension being less than 1/5 of the wavelength of the electromagnetic wave.

Such a small thermal source of radiation has the advantage of being able to be positioned within the evanescent field of the waveguide, creating a strong overlap between the near-field of the emitter and the waveguide mode. It also acts as a partially polarized source of radiation due to the small extension relative to the wavelength. This may be used to excite a preferred mode of propagation in the waveguide.

The thermal source of radiation may be positioned within one wavelength of the electromagnetic wave from the waveguide, in a cross-section of the waveguide, such that to excite a preferred mode of propagation in the waveguide, preferably within 1/5 of the wavelength of the electromagnetic wave from the waveguide.

The thermal source of radiation may be abutting the waveguide or wherein the thermal source of radiation is spaced apart from the waveguide.

The advantage of having the thermal source of radiation abutting the waveguide is that the waveguide will act to conduct heat from the radiation source. Thereby the frequency of excitation of the thermal source of excitation may be high. On the other hand, having the thermal source of radiation spaced apart from the waveguide may reduce the thermal mass and thus increase energy efficiency.

The sensor device may comprise a detecting element positioned such that to couple an electromagnetic wave from the waveguide to the detecting element. The detecting element can be a thermal or semiconductor based photon detector.

Thus the electromagnetic wave propagated through the waveguide may be coupled from the waveguide to the detecting element to detect any absorption by components of gas surrounding the waveguide.

The detecting element may be positioned within one wavelength of the electromagnetic wave from the waveguide, in a cross-section of the waveguide, such that to detect a preferred mode of propagation in the waveguide, preferably within 1/10 of the wavelength of the electromagnetic wave from the waveguide.

Thus the coupling between a preferred mode of propagation in the waveguide and the detecting element may be improved.

The detecting element may be abutting the waveguide, thus increasing the frequency range of detection. Alternatively, the detecting element may be spaced apart from the waveguide, thus reducing the thermal mass of the element.

The waveguide may comprise a periodic structure, preferably a structure which is periodic in the length direction of the waveguide.

Thus the structure may act as a grating to direct the propagating electromagnetic wave in a desired direction. The grating may be used to direct electromagnetic waves into a direction of the waveguide, e.g. when coupling electromagnetic energy from a thermal source of excitation into the waveguide. The grating may be used to direct electromagnetic waves out from the waveguide, e.g. when coupling electromagnetic energy from the waveguide to a detecting element.

The periodic structure may comprise diffractive elements, such as recesses or openings in the waveguide, variations in dimensions of the waveguide, material variations of the waveguide, or structures deposited onto the waveguide.

The periodic structure may be used as a wavelength filter, by directing light of a particular wavelength backwards or out of the waveguide, while selectively permitting transmission of other wavelengths.

The thermal source of radiation and/or the detecting element may be comprised in the periodic structure. The detecting element may have an extension being less than 1/5 of the wavelength of the electromagnetic wave. Thus the detecting element may be incorporated in the periodic structure.

This may be used to increase the coupling of electromagnetical between the thermal source of radiation and/or detecting element and the waveguide.

The waveguide may be of single crystalline silicon, having a high refractive index and low optical losses in the wavelength range of 0.4-10 µm, or even less at 1.2-7 µm. Alternatively, the waveguide may comprise other material such as germanium, silicon germanium, silicon nitride, sapphire, and diamond.

The waveguide may be of a material of a first composition and the support may be of a material of a second composition. The index of refraction in the first material may be higher than the index of refraction in the second material, at the wavelength of the electromagnetic wave. The material of the first composition may be e.g. single crystalline silicon and the material of the second composition may be silicon dioxide.

The material of the first composition may be chosen independently of the material in the second composition.

As stated above the material of the first composition may be chosen from germanium, silicon germanium, silicon nitride, sapphire, and diamond.

Thus optical losses between the waveguide and the support may be reduced.

The substrate, the support and the waveguide may be formed from a SOI wafer comprising a silicon substrate, a silicon dioxide layer and a silicon device layer, wherein the silicon substrate of the SOI wafer forms the substrate of the device, the silicon dioxide layer of the SOI wafer forms the support of the device and the silicon device layer of the SOI wafer forms the waveguide of the device.

The waveguide and the support may form a T-shaped cross-sectional structure.

Thus the waveguide may be supported while reducing optical losses between the waveguide and the support.

The wavelength of the electromagnetic wave may be within the range of 0.4-10, preferably within the range of 1.2-7 µm. More preferred the wavelength of the electromagnetic wave is within the range of 3-7 µm. In the wavelength range of 3-7 µm it is important to minimize the influence of the support.

Thus the electromagnetic wave may be used to detect one or more components in the material surrounding the waveguide. The material surrounding the waveguide may be e.g. a gas or a liquid.

The invention further relates to a gas sensor device comprising a sensor device as disclosed herein for detecting at least one component in gas in contact with the waveguide. The at least one component in gas comprises carbon monoxide, carbon dioxide, dinitrogen oxide, water vapor, hydrocarbons, ammonia, chlorofluorocarbons and/or CFS:s. The sensor device may alternatively be a liquid sensor device comprising a sensor device as disclosed herein for detecting at least one component in liquid in contact with the waveguide.

The invention further relates to a method of detecting a component in gas comprising;
providing a sensor device according to any one of the preceding claims,
providing the gas in contact with the waveguide,
transmitting an electromagnetic wave into a first portion of the waveguide,
allowing the electromagnetic wave interact with the gas in a region of an evanescent wave of the electromagnetic wave around the waveguide,
detecting the electromagnetic wave at a second portion of the waveguide, and
detecting a component in the gas based on the detected electromagnetic wave.

Thus the component in the gas may be detected even in low gas volumes and/or low gas flow.

Alternatively, the invention relates to a corresponding method of detecting a component in liquid in contact with the waveguide.

The sensor device may comprise a thermal source of radiation positioned such that to couple an electromagnetic wave from the source into the waveguide, the source having an extension being less than ⅕ of the wavelength of the electromagnetic wave, wherein the electromagnetic wave is provided by exciting the thermal source of radiation with an alternating current, wherein the alternating current has a frequency which is higher than the thermal cut-off frequency of the heat conduction and/or convection path from source to detector, thereby preventing the propagation of heat waves from source to detector while permitting the propagation of electromagnetic radiation. The heat can be conducted and or convected not only through the waveguide but also through the substrate and even the air.

The invention further relates to a method of fabricating a sensor device as disclosed herein comprising;
providing a wafer,
fabricating the waveguide in the wafer, and
fabricating the support structure in the wafer.

By using a planar wafer of material the sensor device may be miniaturized and batch fabricated in the wafer. Thus the fabrication cost may be reduced by fabricating a wafer with several devices at the same time.

The method may comprise;
providing a wafer comprising a substrate layer, an intermediate layer and a device layer,
fabricating the waveguide in the device layer, and
fabricating the support structure in the intermediate layer, wherein the substrate layer forms the substrate of the device.

Thereby the different layers provide for simple fabrication of the different components of the device (i.e. waveguide, support structure and substrate). The different layers may be optimized for the purpose of fabricating and/or operating the sensor device, e.g. the material of the device layer may be selected for having suitable optical properties, the material in the intermediate layer may be selected for having optical properties which reduces optical losses through the support. The materials in the device and intermediate layers may be selected to have materials properties with suitable fabrication selectivity, e.g. suitable etch selectivity if the device is fabricated by wet or dry etching.

The waveguide may be formed in the device layer by etching and wherein the support structure is formed in the intermediate layer by under-etching the waveguide.

Thus the sensor device may be fabricated by relatively simple fabrication technology suitable for batch processing.

The waveguide may be protected from the under-etching by etch selectivity of materials, by depositing protective layers etcetera.

The wafer may be a SOI wafer comprising a silicon substrate, a silicon dioxide layer and a silicon device layer, wherein the silicon substrate of the SOI wafer corresponds to the substrate layer, the silicon dioxide layer of the SOI wafer corresponds to the intermediate layer and the silicon device layer of the SOI wafer corresponds to the device layer.

Thus the materials of the wafer is suitable for batch fabrication and operation of sensor devices as disclosed herein. The silicon device layer has suitable optical properties in the infrared region, the intermediate silicon dioxide layer has suitable optical properties to reduce optical losses, and the materials provide for an etch selectivity, e.g. by etching the silicon dioxide by buffered hydrofluoric acid (BHF), where the etch selectivity is very high.

The waveguide may be protected from etching, and wherein the support structure is etched after fabricating the waveguide. The waveguide may be protected from etching by an etch stop material or by doping.

BRIEF DESCRIPTION OF DRAWINGS

Various embodiments of the invention will now be described with reference to the appended drawings, where.

DETAILED DESCRIPTION OF EMBODIMENTS

Figure 1:
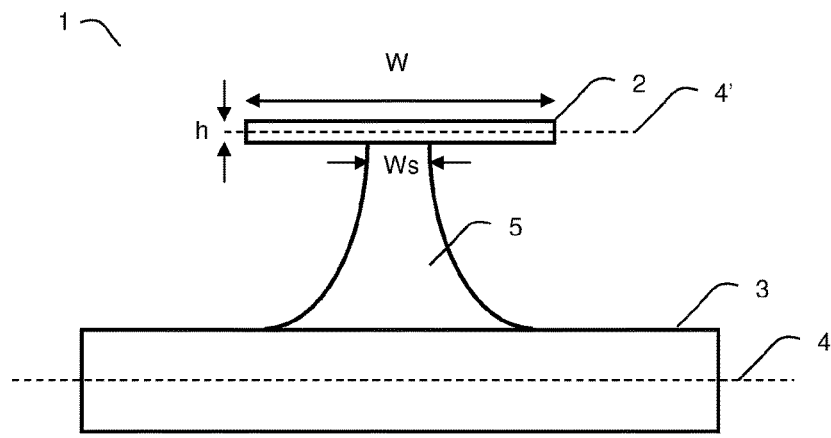
FIG. 1 shows a cross-sectional view of a waveguide supported by a substrate.

The invention relates to a sensor device comprising a waveguide for guiding an electromagnetic wave having a wavelength $\lambda$. The wavelength of the electromagnetic wave is within the range of 0.4-10 µm, preferably within the range of 1.2-7 µm. In FIG. 1 a cross-section of a portion of a waveguide 2 of the sensor device 1 according to one embodiment is shown. The device comprises a substrate 3 forming a support for the sensor device. The substrate is in the form of a planar wafer of material and defines a substrate plane 4. The waveguide extends in a length direction in a waveguide plane 4' parallel to the substrate plane 4, i.e. perpendicular to the cross-sectional view of FIG. 1.

The waveguide has a width W in the waveguide plane in a direction perpendicular to the length direction, and a height h out of the waveguide plane in a direction perpendicular to the length direction. An important feature of the waveguide is that width to height ratio W/h is more than 5. Due to these dimensional features the waveguide may be fabricated with planar fabrication technologies from a wafer of material, such as silicon. The major surfaces of the waveguide, i.e.

extending over the width of the waveguide, may thus be made very smooth. The minor surfaces of the waveguide, i.e. extending over the height of the waveguide, have less impact of the optical performance of the waveguide due to the dimensional features the waveguide. These minor surfaces are more irregular than the major surfaces due to manufacturing issues.

The waveguide 2 is supported on the substrate 3 by a support structure 5 extending from the substrate to the waveguide, along the length direction of the waveguide. The support structure 5 has a width Ws at the point of support of the waveguide, which is smaller than the width W of the waveguide. Thus the optical losses through the support structure 5 may be reduced. In the embodiment shown the width of the support increases gradually towards the substrate, which provides for a mechanically more robust construction.

The height h of the waveguide is less than the wavelength X of the electromagnetic wave which the waveguide is designed to guide. Thus a waveguide is provided which may be used to guide an electromagnetic wave, having a large portion of the energy propagating as an evanescent wave, with low levels of optical losses in the waveguide.

Figure 2:
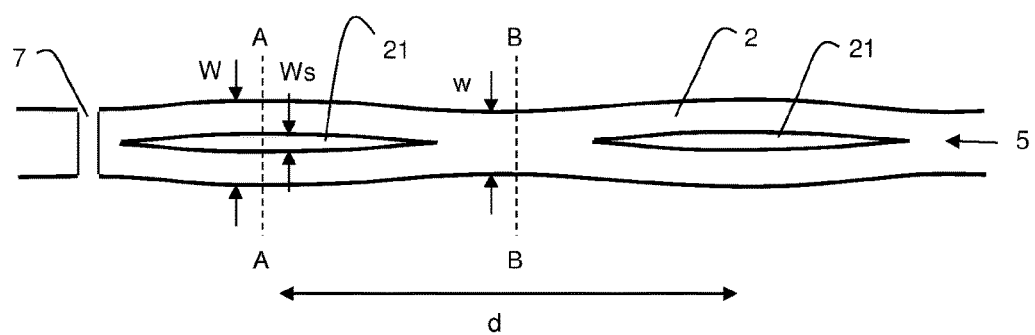
FIG. 2 shows a cross-sectional view of a waveguide free-hanging over a substrate.

The width of the waveguide may be varied along the length direction of the waveguide. This is illustrated in FIG. 2, where the waveguide is shown from above. The cross-section shown in FIG. 1 corresponds to the plane A-A, having a width W of the waveguide. By using microfabrication technologies for fabricating the device, e.g. wet or dry etching of material, the width of the support varies correspondingly with the along the length direction of the waveguide. Thus at another portion of the waveguide, at B-B, the width of the waveguide is w, which is less than W. The width Ws of the support structure 5 has then decreased to render the waveguide free hanging. The waveguide is free hanging along a plurality of portions of the length direction, so that a plurality of support pillars 21 are formed. Thus the support structure 5 comprises a plurality of support pillars 21. The distance d from the center of a support pillar to the center of an adjacent support pillar 21, i.e. the center-to-center distance, varies along the length direction. By having the center-to-center distance d varying, unwanted constructive or destructive interferences between the propagating wave and the waves reflected at the supports may be avoided. The center-to-center distance d between the support pillars may be randomized.

Figure 3:
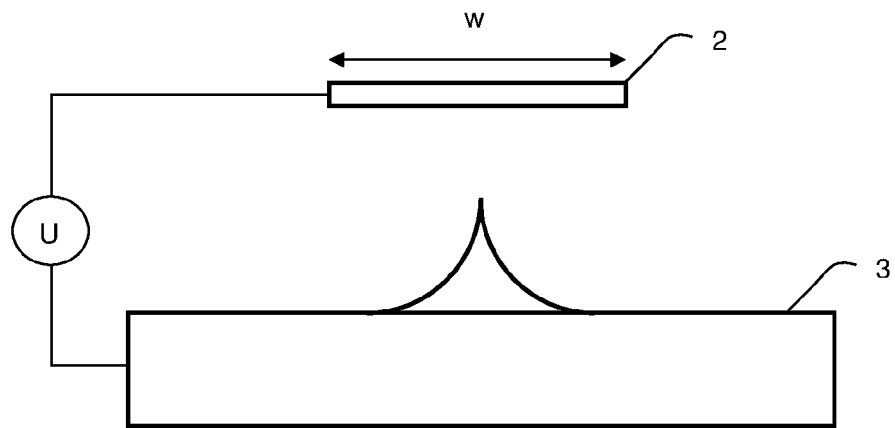
FIG. 3 shows a top view showing a portion of a waveguide having supported and free-hanging sections.

In FIG. 3 a cross-section of a portion of a waveguide 2 of the sensor device corresponding to the section B-B in FIG. 2 is shown. The width of the waveguide 2 is w, and the height is h. The support structure 5 extending from the substrate 3 has been reduced when compared to FIG. 1 by reducing the width of the waveguide. Thus a waveguide may be provided which is supported along at least a first portion of the length direction, and that the waveguide is free hanging along at least a second portion of the length direction.

Further, in FIG. 3 it is shown that the sensor device the device may comprise means to apply a force to the free hanging portion of the waveguide. This is shown as a means to apply a voltage potential between the substrate and the free hanging portion of the waveguide. Such a force may be used to deflect the waveguide, which may be used to modulate the electromagnetic wave propagated through the waveguide.

As further shown in FIG. 2 the waveguide may comprise one or more gaps 7 along the length direction of the waveguide. The gaps are less than the wavelength of the electromagnetic wave, preferably less than ⅕ of the wavelength of the electromagnetic wave. The gaps may be used as obstacles for heat or electricity, while still providing for propagation of the electromagnetic waves.

Figure 4:
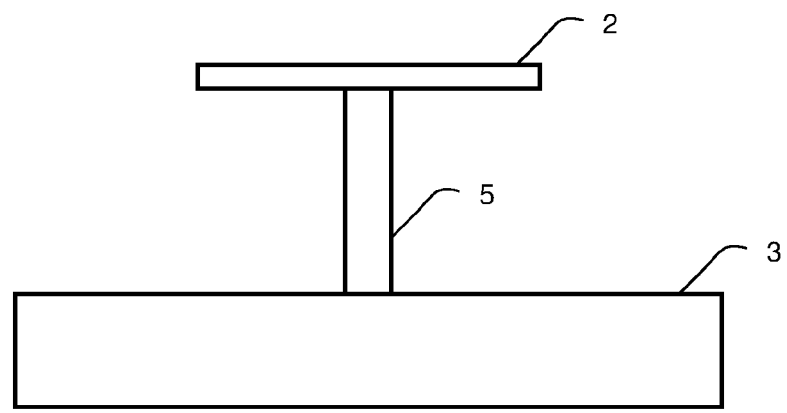
FIG. 4 shows a cross-sectional view of another waveguide supported by a substrate.

The waveguide and the support forms a T-shaped cross-sectional structure, as shown in FIG. 1. According to one embodiment the support structure 5 has a uniform width in a cross section of the waveguide, forming a T-shape as shown in FIG. 4.

Figure 5:
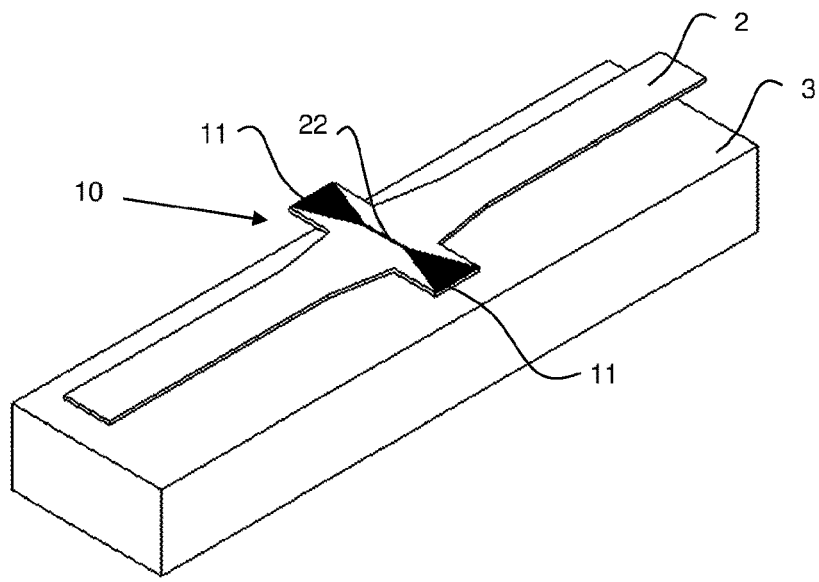
FIG. 5 shows a thermal source of radiation and a detecting element.

In FIG. 5 an example of a thermal source of radiation 10 integrated on a section of a waveguide 2. The thermal source of radiation comprises a wire source extending across the waveguide and connected to a pair of electrical connecting pads 11 for connecting an electrical current source. The wire has a length extending across the waveguide and a width being less than ⅕ of the wavelength of the electromagnetic wave. The thermal source of radiation is positioned on the surface of the waveguide such that to couple an electromagnetic wave from the source into the waveguide. Thus the source is positioned within one wavelength of the electromagnetic wave from the waveguide such that to excite a preferred mode of propagation in the waveguide.

In a similar manner the sensor device comprises a detecting element positioned such that to couple an electromagnetic wave from the waveguide to the detecting element. FIG. 5 may be used to illustrate a bolometric detecting element, since the construction is similar to the thermal source of radiation. The detecting element is positioned within one wavelength of the electromagnetic wave from the waveguide, in a cross-section of the waveguide, such that to detect a preferred mode of propagation in the waveguide, preferably within ⅕ of the wavelength of the electromagnetic wave from the waveguide. The detecting element is abutting the waveguide or is spaced apart from the waveguide.

Figure 6:
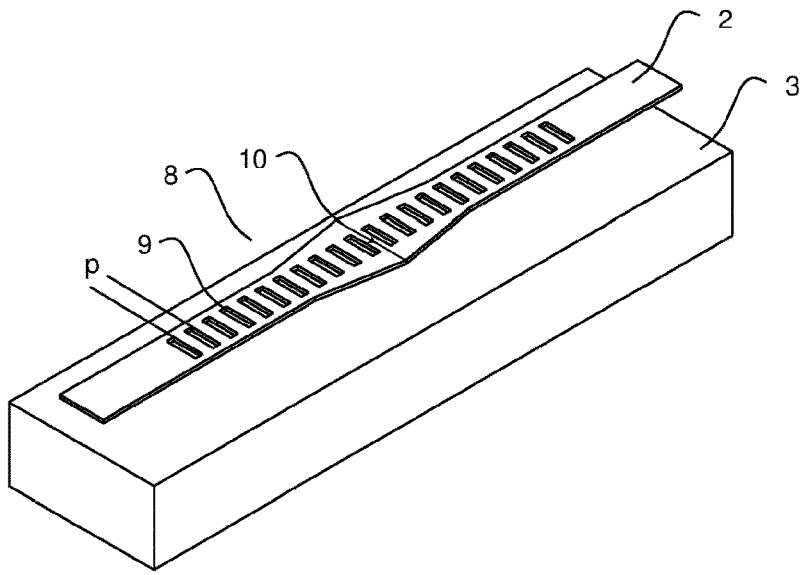
FIG. 6 shows a portion of a waveguide having a periodic structure and a source of radiation.

As shown in FIG. 6 the waveguide 2 may comprise a structure 8 being periodic in the length direction of the waveguide, as shown as a plurality of diffractive elements in the form of cut-out openings 9 having a period p. Alternatively the diffractive elements may comprise recesses or openings in the waveguide, variations in dimensions of the waveguide, material variations of the waveguide, or structures deposited onto the waveguide. The periodic structure 8 may include the source of radiation 10, and periodic structure may function as a grating having a period may be configured to direct the electromagnetical energy in the length direction of the waveguide. Similarly, the detecting element may be comprised in the periodic structure.

The material of the waveguide 2 may be single crystalline silicon, having good optical properties in the wavelength range of 0.4-10 µm, or even better at the wavelength range of 1.2-7 µm. It is conceived that the waveguide is of a material of a first composition and the support structure 5 is of a material of a second composition. Preferably the index of refraction in the first material is higher than the index of refraction in the second material, at the wavelength of the electromagnetic wave. The support structure 5 may thus e.g. be of silicon dioxide, which due to the differences in refractive index will reduce optical losses from the waveguide to the support structure.

According to one example the substrate 3, the support structure 5 and the waveguide 2 of the sensor device is formed from a silicon on insulator (SOI) wafer comprising a silicon substrate, a silicon dioxide layer and a silicon device layer. The silicon substrate of the SOI wafer forms the substrate of the device, the silicon dioxide layer of the SOI wafer forms the support structure 5 of the device and the silicon device layer of the SOI wafer forms the waveguide of the device.

Figure 7A:
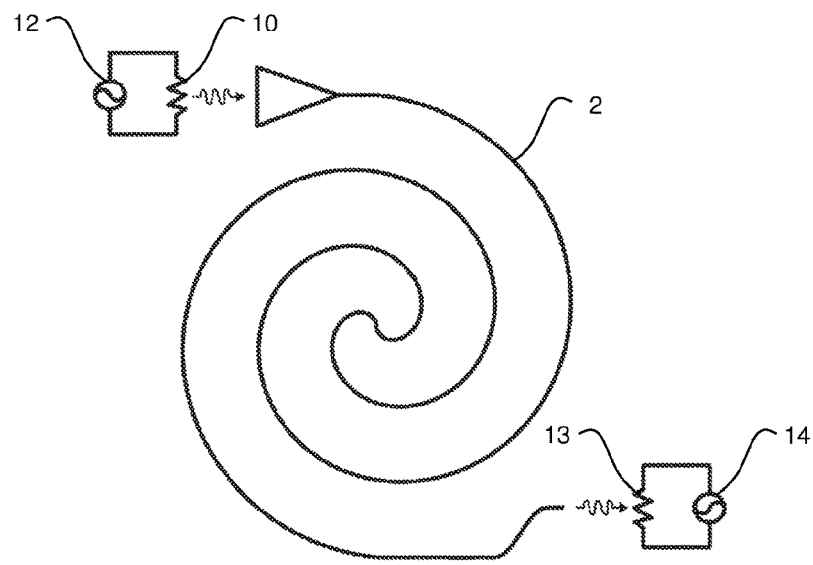
FIG. 7 shows two examples of a gas sensor device comprising a waveguide, a thermal source of radiation and at least one detecting element.
Figure 7B:
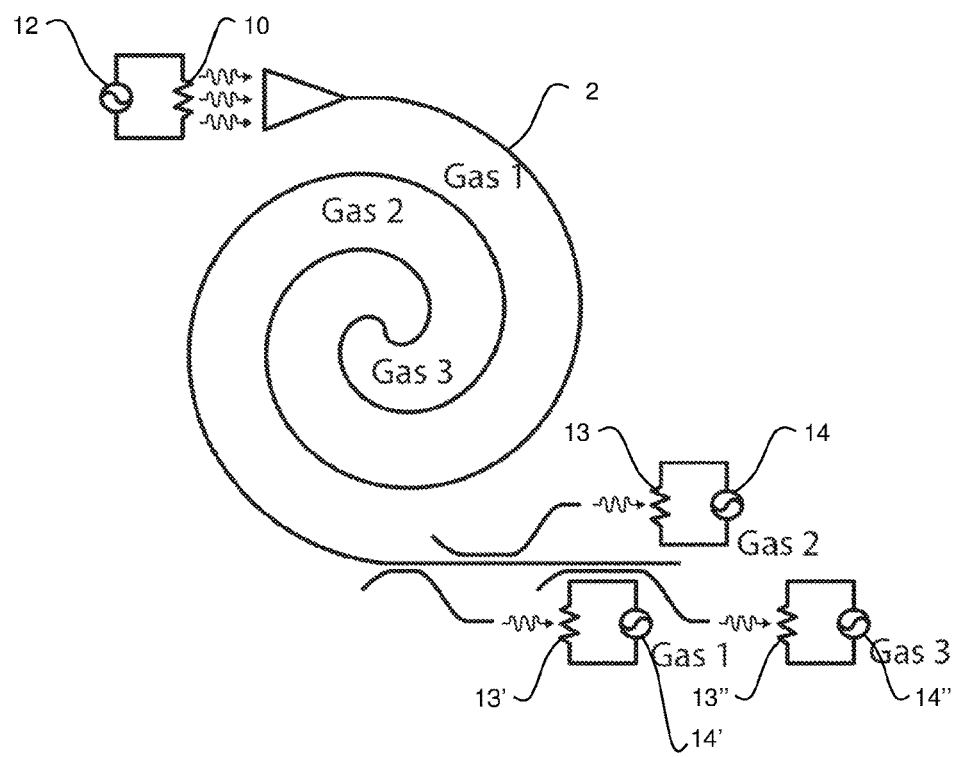

In FIG. 7 two examples of a gas sensor device comprising a sensor device for detecting at least one component in gas is shown. In FIG. 7(*a*) a gas sensor device for detecting one component in gas. The sensor device comprises a waveguide 2, on a support structure 5 as previously discloses, formed as a double spiral and thus providing a very long waveguide on a small area. As an alternative the waveguide may have a meander shape or other spiral shapes. The sensor device further comprises a thermal source of radiation 10 at a first portion of the waveguide and a detecting element 13 on a second portion of the waveguide. The radiation source is driven by a current source 12 to generate an electromagnetic wave of a specified frequency, which is coupled into the waveguide. The electromagnetic wave propagates along the waveguide, having a large portion of the energy propagating as an evanescent wave in the space surrounding the waveguide. In this space, and in the region of the evanescent wave along the waveguide, any component of gas having a peak of absorption corresponding to the wavelength of the electromagnetic wave will absorb energy from the propagating wave. The amount of energy in the electromagnetic wave at the selected frequency will be detected by the detecting element and will be a measure of the amount and/or presence of the component of gas.

In FIG. 7(*b*) a similar gas sensor device for detecting three different components of gas (gas 1, gas 2 and gas 3) is shown. The gas sensor device differs from what is shown in FIG. 7(*a*) in that the thermal source of radiation is configured to emit electromagnetic waves of several wavelengths, corresponding to absorption peaks for more than one component of gas. The presence (and amount) of any of the three components of gas (gas 1, gas 2 and gas 3) in the region of the evanescent wave of the electromagnetic waves along the waveguide, will be detected as an absorption of energy. Each component of gas may be detected by a dedicated detecting element 13, 13', 13". The detecting elements may be coupled to the waveguide by wavelength selecting devices, such as gratings, to tap off a selected wavelength of the propagating electromagnetic wave.

Figure 8:
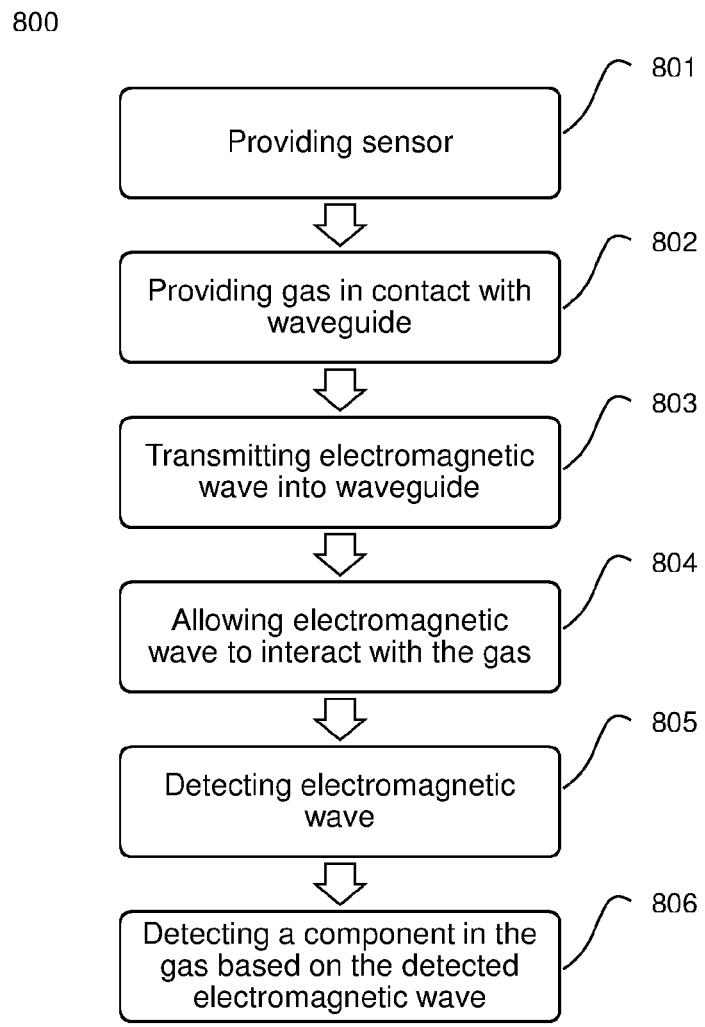
FIG. 8 shows a method of detecting a component in gas.

Having a sensor device as disclosed, a method of detecting a component in gas is illustrated in FIG. 8. The method 800 comprises the steps of providing a sensor 801 as disclosed herein, providing gas in contact with the waveguide 802 and transmitting an electromagnetic wave into the first portion of the waveguide 803. The electromagnetic wave propagates through the waveguide, having a large portion of the electromagnetic energy propagating as an evanescent wave along the waveguide. This evanescent wave interacts 804 with the gas in a region around the waveguide, which absorbs energy at specific frequencies of the electromagnetic wave. The electromagnetic wave is thereafter detected 805 by the detecting element at a second portion of the waveguide. From the specific spectrum of absorption a component in the gas may be detected 806.

The sensor device 1 comprises a thermal source of radiation 10 as shown in FIG. 5 positioned such that to couple an electromagnetic wave from the source into the waveguide. The source has an extension being less than ⅕ of the wavelength of the electromagnetic wave. The electromagnetic wave is provided by exciting the thermal source of radiation with an alternating current, wherein the alternating current has a frequency which is higher than the thermal cut-off frequency of the heat conduction and/or convection path from source to detector, thereby preventing the propagation of heat waves from source to detector while permitting the propagation of electromagnetic radiation.

The component in gas may e.g. comprise carbon monoxide, carbon dioxide, dinitrogen oxide, water vapor, hydrocarbons, ammonia and/or chlorofluorocarbons.

Figure 9:
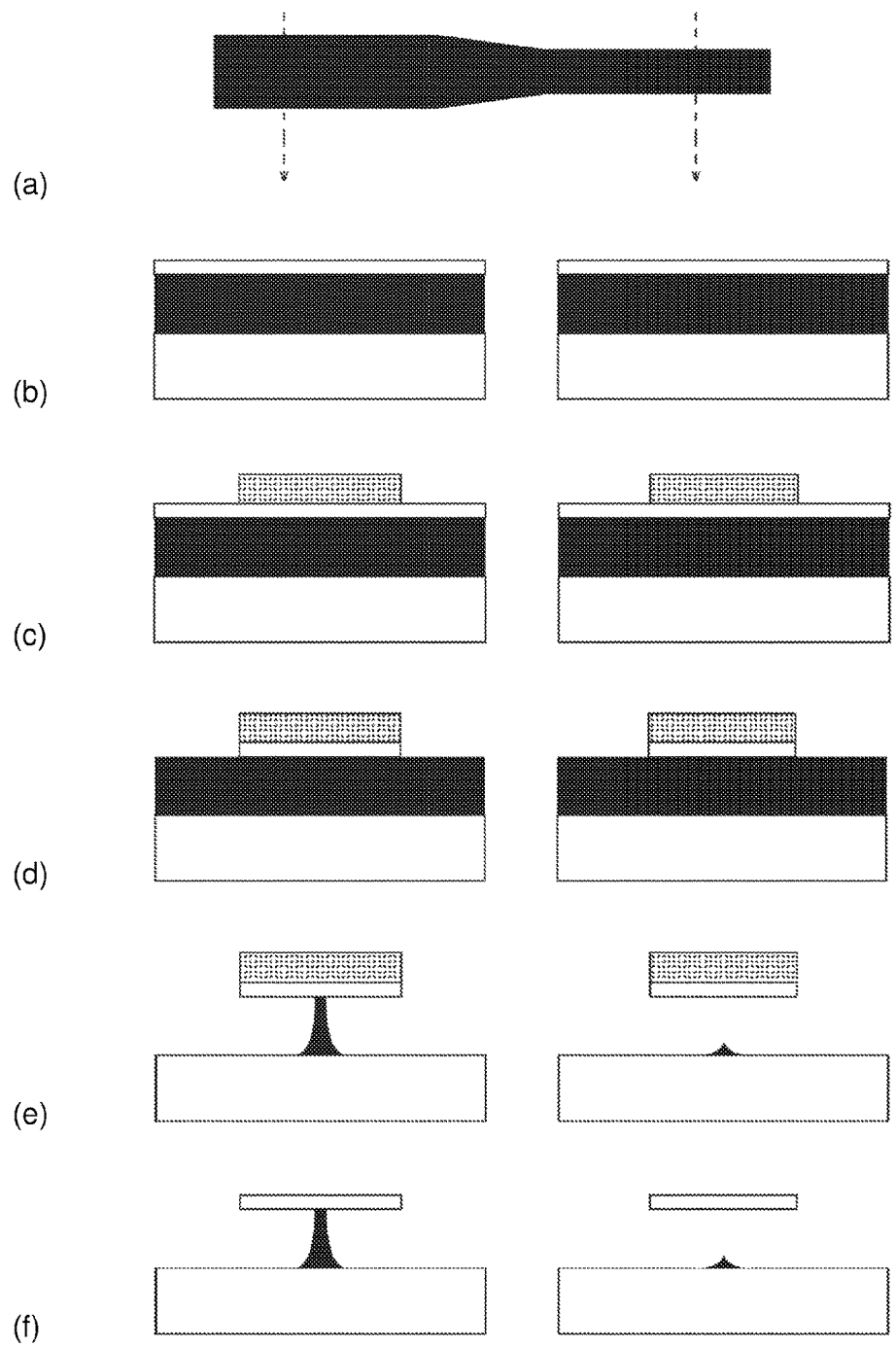
FIG. 9 shows a method of fabricating a sensor device.

In FIG. 9 a method of fabricating a sensor device (a) is disclosed. The method comprises the step (b) of providing a wafer comprising a substrate layer, an intermediate layer and a device layer. The wafer may be a SOI wafer comprising a silicon substrate, a silicon dioxide layer and a silicon device layer. The waveguide is fabricated in the device layer by lithography and dry etching with photoresist as etch mask, (c) and (d). The support structure 5 is fabricated in the intermediate layer (e) by wet isotropic etching, i.e. under-etching of the waveguide. Finally, the photoresist etch mask is removed (f). Depending on the width of the waveguide, the width of the support structure 5 may be controlled, as illustrated by the left- and right hand side of the drawing, and the waveguide may be made free hanging at portions along the waveguide. The substrate layer of the wafer forms the substrate of the device. The silicon substrate of the SOI wafer corresponds to the substrate layer, the silicon dioxide layer of the SOI wafer corresponds to the intermediate layer and the silicon device layer of the SOI wafer corresponds to the device layer.

Alternatively, the waveguide and support structure 5 may be fabricated by fabricating the waveguide and protecting the waveguide from etching by depositing an etch stop material. Thereafter the support structure 5 may be etched. As a further alternative the material for forming the waveguide in the wafer may be doped such that to provide an etch selectivity for the etching of the waveguide and surrounding material.

The invention claimed is:

1. A sensor device comprising;
a planar substrate defining a substrate plane,
a waveguide for guiding an electromagnetic wave, the waveguide extending in a length direction in a waveguide plane parallel to the substrate plane, the waveguide having a width in the waveguide plane in a direction perpendicular to the length direction, and a height out of the waveguide plane in a direction perpendicular to the length direction, wherein the width to height ratio is more than 5,
wherein the height of the waveguide is less than the wavelength of the electromagnetic wave,
wherein the waveguide is supported on the substrate by a support structure extending from the substrate to the waveguide, along the length direction of the waveguide, having a width which is smaller than the width of the waveguide, at the point of support of the waveguide, wherein the width of the waveguide is varied along the length direction of the waveguide, and wherein the width of the support structure varies correspondingly along the length direction of the waveguide, and wherein the waveguide is of a material of a first composition and the support structure is of a material of a second composition.

2. The sensor device according to claim 1, wherein the waveguide is supported along at least a first portion of the length direction, and wherein the width of the waveguide and thus the support structure is decreased such that the waveguide is free hanging along at least a second portion of the length direction.

3. The sensor device according to claim 2, wherein the waveguide is free hanging along a plurality of portions of the length direction, so that a plurality of support pillars are formed, wherein the distance from the center of a support pillar to the center of an adjacent support pillar varies along the length direction.

4. The sensor device according to claim 2, wherein the device comprises means to apply a force to the free hanging portion of the waveguide such that to deflect the waveguide.

5. The sensor device according to claim 1, wherein the waveguide comprises at least one gap along the length direction of the waveguide, the at least one gap being less than the wavelength of the electromagnetic wave.

6. The sensor device according to claim 1, wherein the device comprises a thermal source of radiation positioned such that to couple an electromagnetic wave from the source into the waveguide, the source having a length which is less than 1/5 of the wavelength of the electromagnetic wave.

7. The sensor device according to claim 6, wherein the thermal source of radiation is positioned within one wavelength of the electromagnetic wave from the waveguide, in a cross-section of the waveguide, such that to excite a preferred mode of propagation in the waveguide.

8. The sensor device according to claim 6, wherein the thermal source of radiation is abutting the waveguide or wherein the thermal source of radiation is spaced apart from the waveguide.

9. The sensor device according to claim 1, wherein the device comprises a detecting element positioned so as to couple an electromagnetic wave from the waveguide to the detecting element.

10. The sensor device according to claim 9, wherein the detecting element is positioned within one wavelength of the electromagnetic wave from the waveguide, in a cross-section of the waveguide, so as to detect a preferred mode of propagation in the waveguide.

11. The sensor device according to claim 9, wherein the detecting element is abutting the waveguide or wherein the detecting element is spaced apart from the waveguide.

12. The sensor device according to claim 9, wherein the detecting element has a length which is less than 1/5 of the wavelength of the electromagnetic wave.

13. The sensor device according to claim 1, wherein the waveguide comprises a periodic structure.

14. The sensor device according to claim 13, wherein the periodic structure comprises diffractive elements.

15. The sensor device according to claim 13, wherein the device comprises: (i) a thermal source of radiation positioned such that to couple an electromagnetic wave from the source into the waveguide, and (ii) a detecting element positioned such that to couple an electromagnetic wave from the waveguide to the detecting element, and wherein the thermal source of radiation and/or the detecting element is comprised in the periodic structure.

16. The sensor device according to claim 1, wherein the index of refraction in the first material is higher than the index of refraction in the second material, at the wavelength of the electromagnetic wave.

17. The sensor device according to claim 1, wherein the substrate, the support structure and the waveguide is formed from a SOI wafer comprising a silicon substrate, a silicon dioxide layer and a silicon device layer, wherein the silicon substrate of the SOI wafer forms the substrate of the device, the silicon dioxide layer of the SOI wafer forms the support structure of the device and the silicon device layer of the SOI wafer forms the waveguide of the device.

18. The sensor device according to claim 1, wherein the waveguide and the support structure forms a T-shaped cross-sectional structure.

19. The sensor device according to claim 1, wherein the wavelength of the electromagnetic wave is within the range of 0.4-10 μm.

20. A gas sensor device comprising a sensor device according to claim 1, for detecting at least one component in a fluid.

21. The gas sensor device according to claim 20 wherein the at least one component in gas comprises carbon monoxide, carbon dioxide, dinitrogen oxide, water vapor, hydrocarbons, ammonia, chlorofluorocarbons and/or CFS:s.

22. A method of detecting a component in a fluid comprising;
providing a sensor device according to claim 1,
providing the fluid in contact with the waveguide,
transmitting an electromagnetic wave into a first portion of the waveguide, allowing the electromagnetic wave interact with the fluid in a region of an evanescent wave of the electromagnetic wave around the waveguide,
detecting the electromagnetic wave at a second portion of the waveguide, and detecting a component in the gas based on the detected electromagnetic wave.

23. The method according to claim 22, wherein the sensor device comprises a thermal source of radiation positioned such that to couple an electromagnetic wave from the source into the waveguide, the source having a length which is less than 1/5 of the wavelength of the electromagnetic wave,
wherein the electromagnetic wave is provided by exciting the thermal source of radiation with an alternating current, wherein the alternating current has a frequency which is higher than the thermal cut-off frequency of the heat conduction and/or convection path from source to detector, thereby preventing the propagation of heat waves from source to detector while permitting the propagation of electromagnetic radiation.

24. A method of fabricating a sensor device according to claim 1, comprising;
providing a wafer,
fabricating the waveguide in the wafer, and
fabricating the support structure in the wafer.

25. The method according to claim 24, comprising;
providing a wafer comprising a substrate layer, an intermediate layer and a device layer,
fabricating the waveguide in the device layer, and
fabricating the support structure in the intermediate layer,
wherein the substrate layer forms the substrate of the device.

26. The method according to claim 25, wherein the waveguide is formed in the device layer by etching and wherein the support structure is formed in the intermediate layer by under-etching the waveguide.

27. The method according to claim 25, wherein the wafer is a SOI wafer comprising a silicon substrate, a silicon dioxide layer and a silicon device layer, wherein the silicon substrate of the SOI wafer corresponds to the substrate layer, the silicon dioxide layer of the SOI wafer corresponds to the intermediate layer and the silicon device layer of the SOI wafer corresponds to the device layer.

28. The method according to claim 24, wherein the waveguide is protected from etching, and wherein the support structure is etched after fabricating the waveguide.

29. The method according to claim 28, wherein the waveguide is protected from etching by an etch stop material.

30. The method according to claim 28, wherein the waveguide is protected from etching by doping.

* * * * *